ulus007731516B2

United States Patent
Puttinger et al.

(10) Patent No.: US 7,731,516 B2
(45) Date of Patent: Jun. 8, 2010

(54) CONNECTOR SYSTEM FOR ENGAGING A PORTION OF A PLUG WITHIN A RECEPTACLE

(75) Inventors: Ferdinand Puttinger, Zipf (AT); Reinhold Bruestle, Zipf (AT); Weston Blaine Griffin, Niskayuna, NY (US); Warren Lee, Niskayuna, NY (US); Douglas Glenn Wildes, Ballston Lake, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 12/207,271

(22) Filed: Sep. 9, 2008

(65) Prior Publication Data

US 2010/0062633 A1 Mar. 11, 2010

(51) Int. Cl.
*H01R 13/15* (2006.01)
(52) U.S. Cl. ...................................... 439/260
(58) Field of Classification Search .................. 439/260, 439/259, 261, 262, 265, 66, 67
See application file for complete search history.

(56) References Cited

U.S. PATENT DOCUMENTS

| 3,922,054 | A | * | 11/1975 | Dechelette | .................. 439/260 |
| 5,368,496 | A | | 11/1994 | Ranalletta et al. | |
| 5,617,866 | A | | 4/1997 | Marian, Jr. | |
| 5,846,097 | A | | 12/1998 | Marian, Jr. | |
| 5,913,688 | A | | 6/1999 | Marian, Jr. | |
| 6,440,076 | B1 | | 8/2002 | Sudol et al. | |
| 6,524,114 | B2 | * | 2/2003 | Watanabe et al. | ............. 439/65 |
| 6,679,714 | B2 | * | 1/2004 | Kimura | ..................... 439/261 |
| 6,884,099 | B1 | * | 4/2005 | Cannon | ..................... 439/318 |
| 6,979,216 | B2 | * | 12/2005 | Maeda et al. | ............... 439/260 |
| 7,182,647 | B2 | * | 2/2007 | Muench et al. | ............. 439/660 |
| 7,249,976 | B1 | * | 7/2007 | Watson | ....................... 439/651 |
| 7,255,678 | B2 | * | 8/2007 | Mehi et al. | .................. 600/446 |

\* cited by examiner

*Primary Examiner*—Chandrika Prasad
(74) *Attorney, Agent, or Firm*—Dean Small; Small Patent Law Group

(57) ABSTRACT

An cable connector system is provided. A receptacle for the connector system includes a pair of opposing compression plates and at least one rotatable member configured to move the opposing compression plates as the rotatable member rotates. The compression plates cause contact with a portion of the plug inserted therebetween.

20 Claims, 16 Drawing Sheets

US 7,731,516 B2

CONNECTOR SYSTEM FOR ENGAGING A PORTION OF A PLUG WITHIN A RECEPTACLE

BACKGROUND OF THE INVENTION

This invention relates generally to connectors and, more particularly to connectors for connecting cables, such as connectors for connecting cables that interconnect components of a medical imaging system.

When interconnecting cables, particularly cables having contacts for high signal counts (e.g., a large number of signal pins), it is important to have proper alignment and contact. As the number of contacts increase, the need for precise alignment increases, especially if the size of the connectors connecting the cables does not increase, thereby having more connections in the same area. Misalignment of the cables can result in damage to the contacts or signal pins, which can result in temporary or permanent transmission problems between the interconnected cables. Also, the more force required to interconnect cables with a connector, the more likely damage will occur to the contacts or signal pins if the cable contacts or signal pins are misaligned. Also, as the number of contacts or signal pins increase and connector sizes decrease, the amount of force needed to interconnect cables with these connectors increases. The increased force needed to interconnect these cables (e.g., high signal count cables) with known connectors, also increases the likelihood of improper connection when not enough force is applied to mate all of the contacts or signal pins.

In certain clinical ultrasound applications, the ultrasound system is not easily accessible, making it difficult for a user to connect the probe to the system. It is known to provide another cable, sometimes referred to as an umbilical cable, that is connected at one end to the ultrasound system and allows connection at the other end to a probe. It is important that the probe connector end of the umbilical cable and the system connector end of the probe align properly when interconnected. Misalignment can cause damage to the connections, as well as cause the system to fail to operate properly. Alignment is also increasingly more important as cables providing high signal counts are used. Moreover, know connectors do not provide adequate blocking mechanisms to prevent misuse and damage of the connector by a user. Additionally, quick interconnection is important to reduce setup time between imaging scans, thereby increasing throughput of, for example, patients to be imaged.

BRIEF DESCRIPTION OF THE INVENTION

In accordance with an embodiment of the invention, a receptacle for a connector system having a plug is provided. The receptacle includes a pair of opposing compression plates and at least one rotatable member configured to move the opposing compression plates as the rotatable member rotates. The compression plates cause contact with a portion of the plug inserted therebetween.

In accordance with another embodiment of the invention, a connector system is provided that includes a plug portion having a connection member and a receptacle portion configured to engage the plug portion. The receptacle portion includes rotationally actuated contact plates movable to engage the connection member of the plug portion.

In accordance with yet another embodiment of the invention, an ultrasound system is provided that includes a control portion having an umbilical cable connected thereto. The umbilical cable includes a receptacle providing high signal count communication. The receptacle includes a rotational actuating mechanism. The ultrasound system further includes an ultrasound probe having a probe cable connected thereto. The probe cable includes a plug and wherein interconnection of the umbilical cable with the probe cable via the receptacle and plug is actuated by the rotational actuating mechanism of the receptacle.

DETAILED DESCRIPTION OF THE INVENTION

Figure 1:
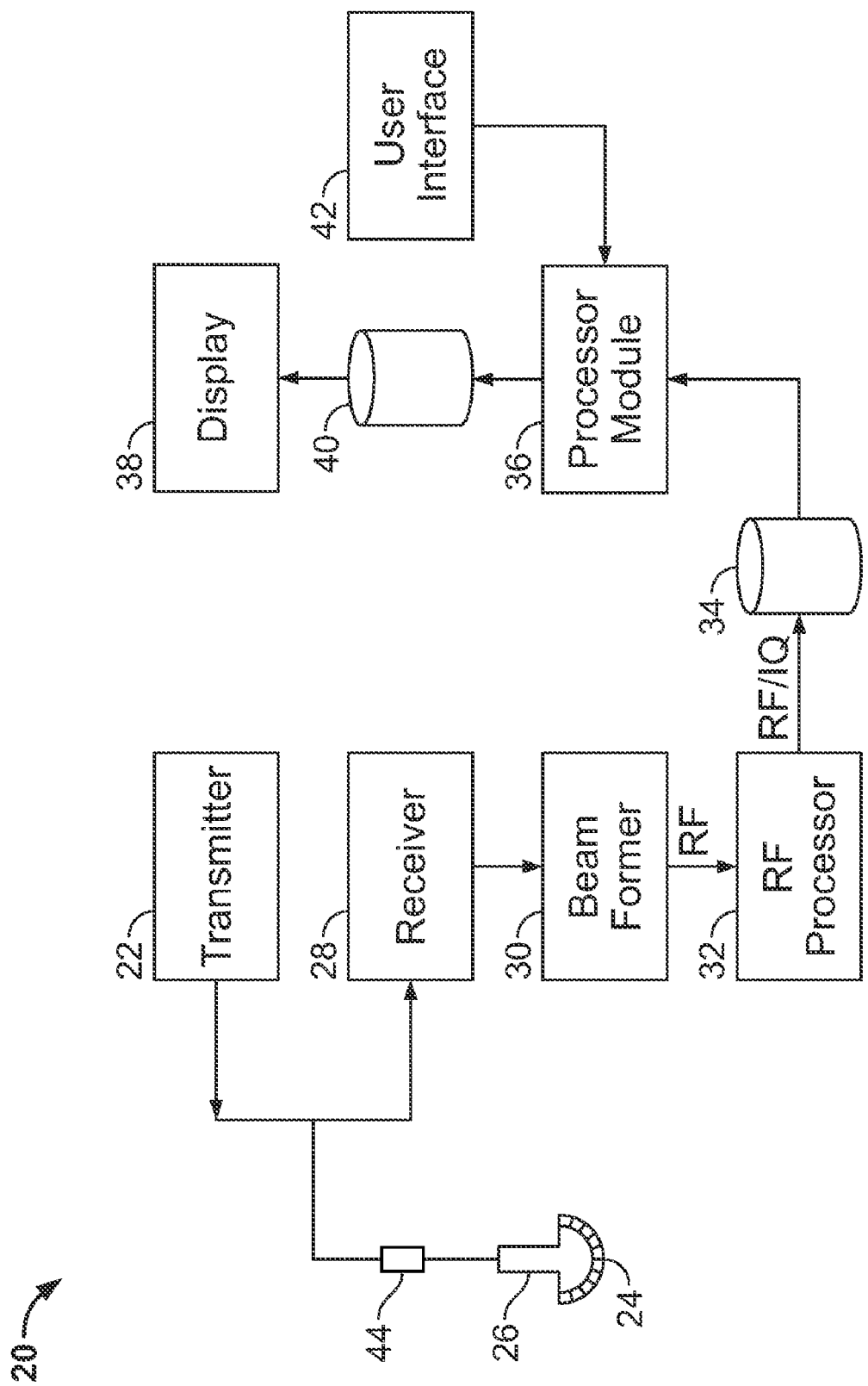
FIG. 1 is a block diagram of an ultrasound system formed in accordance with an embodiment of the invention.

The foregoing summary, as well as the following detailed description of certain embodiments of the invention, will be better understood when read in conjunction with the appended drawings. To the extent that the figures illustrate diagrams of different hardware components or functional blocks, the components or blocks are not necessarily indicative of the division between hardware or different operations. Thus, for example, one or more of the components or blocks may be implemented in a single piece of hardware (e.g., combined into a single piece of hardware) or separated into different components. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

It should be noted that although the various embodiments may be described in connection with an ultrasound system, the various embodiments are not limited to ultrasound imaging or to imaging systems. In particular, the various embodiments may be implemented in connection or combination with different types of medical imaging, including, for example, magnetic resonance imaging (MRI) and computed-tomography (CT) imaging. Further, the various embodiments may be implemented in other non-medical imaging systems, for example, non-destructive testing systems, such as airport screening systems. Moreover, the various embodiments may be implemented in any system wherein interconnection of two cables is desired or needed, for example, wherein a plurality of signal interfaces are interconnected. In general, the various embodiments may be used in any system where interconnection of cables, lines, wires, etc. is needed or desired.

Various embodiments of the invention provide a connector system that may be used, for example, for interconnecting two high signal count cables, such as in ultrasound applications. The connector system provides both alignment and secure connection of the two cables. For example, the connector system may be used to connect an ultrasound probe to an ultrasound system. FIG. 1 is a block diagram of an exemplary ultrasound system 20 in which various embodiments of a connector system may be used and as described in more detail below. The ultrasound system 20 includes a transmitter 22 that drives an array of elements 24 (e.g., piezoelectric crystals) within one or more transducers 26 to emit pulsed ultrasonic signals into a body or volume. It should be noted that with respect to the array of elements 24 in the transducer 26, a variety of different geometries and configurations may be used and the transducers 26 may be provided as part of, for example, different types of ultrasound probes having different connectors as described in more detail below.

The emitted ultrasonic signal are back-scattered from structures in the body, for example, blood cells, muscular tissue, veins or objects within the body (e.g., a catheter or needle) to produce echoes that return to the array of elements 24. The echoes are received by a receiver 28. The received echoes are provided to a beamformer 30 that performs beamforming and outputs an RF signal. The RF signal is then provided to an RF processor 32 that processes the RF signal. Alternatively, the RF processor 32 may include a complex demodulator (not shown) that demodulates the RF signal to form IQ data pairs representative of the echo signals. The RF or IQ signal data may then be provided directly to a memory 34 for storage (e.g., temporary storage).

The ultrasound system 20 also includes a processor module 36 to process the acquired ultrasound information (e.g., RF signal data or IQ data pairs), which may be acquired from an ultrasound probe connected to the transmitter 22 and receiver using a connector 44. The processor module 36 prepares frames of ultrasound information for display on a display 38. The processor module 36 is adapted to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored temporarily in the memory 34 during a scanning session and processed in less than real-time in a live or off-line operation. An image memory 40 is included for storing processed frames of acquired ultrasound information that are not scheduled to be displayed immediately. The image memory 40 may comprise any known data storage medium, for example, a permanent storage medium, removable storage medium, etc.

The processor module 36 is connected to a user interface 42 that controls operation of the processor module 36 and is configured to receive inputs from an operator. The display 38 includes one or more monitors that present patient information, including diagnostic ultrasound images to the user for review, diagnosis and analysis. The display 38 may automatically display, for example, a 3D or 4D ultrasound data set stored in the memory 34 or 40 or currently being acquired. One or both of the memory 34 and the memory 40 may store 3D data sets of the ultrasound data, where such 3D data sets are accessed to present 2D and 3D images. For example, a 3D ultrasound data set may be mapped into the corresponding memory 34 or 40, as well as one or more reference planes. The processing of the data, including the data sets, is based in part on user inputs, for example, user selections received at the user interface 42.

In operation, the system 20 acquires data, for example, volumetric data sets by various techniques (e.g., 3D scanning, real-time 3D imaging, volume scanning, 2D scanning with transducers having positioning sensors, freehand scanning using a voxel correlation technique, scanning using 2D or matrix array transducers, etc.). The data may be acquired by moving the transducer 26, such as along a linear or arcuate path, while scanning a region of interest (ROI). At each linear or arcuate position, the transducer 26 obtains scan planes that are stored in the memory 34. The transducer 26 also may be mechanically moveable within the ultrasound probe to acquire volumetric ultrasound images.

Figure 2:
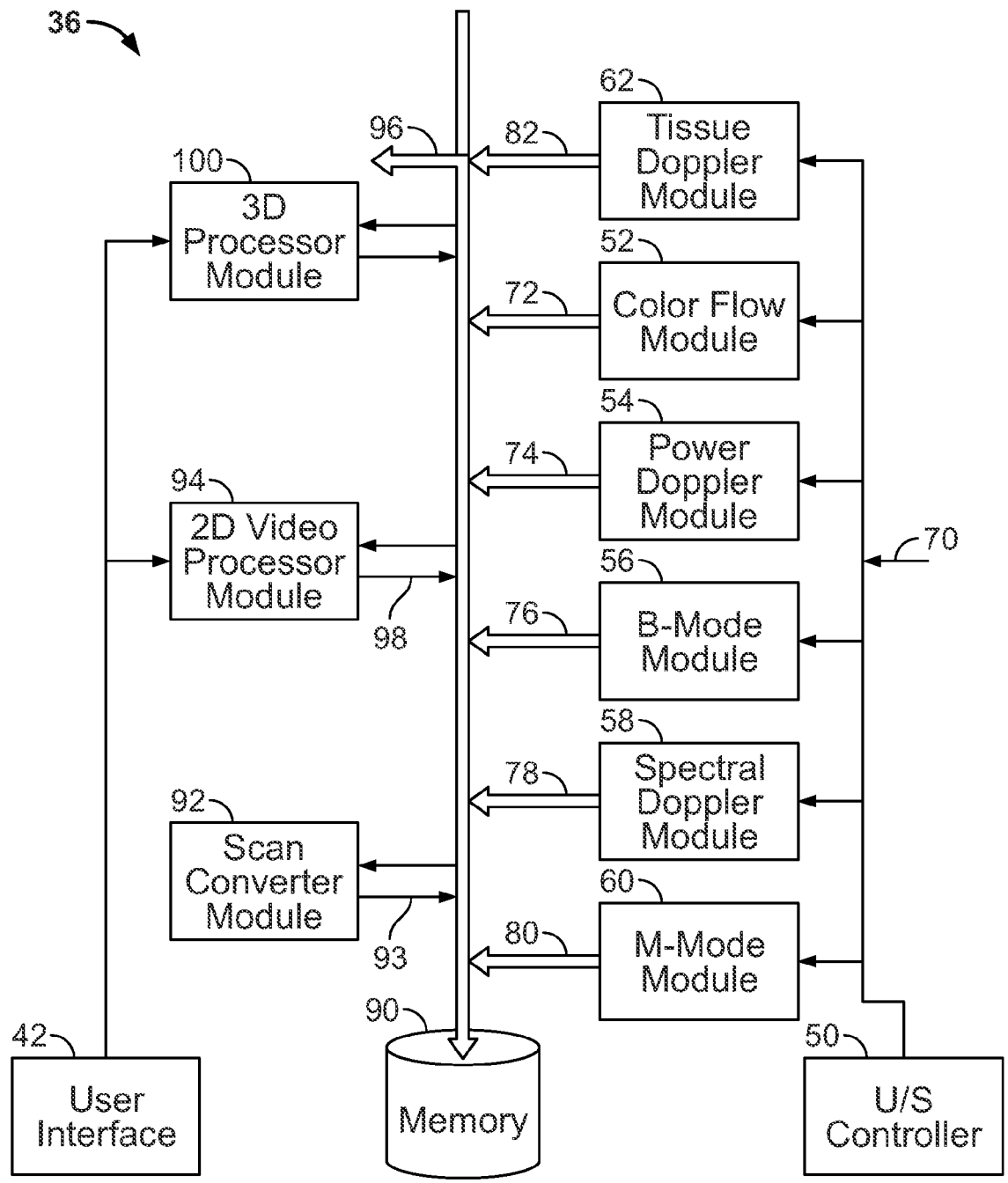
FIG. 2 is a block diagram of an ultrasound processor module of FIG. 1 formed in accordance with an embodiment of the invention.

FIG. 2 is an exemplary block diagram of the ultrasound processor module 36 of FIG. 1. The ultrasound processor module 36 is illustrated conceptually as a collection of sub-modules, but may be implemented utilizing any combination of dedicated hardware boards, DSPs, processors, etc. Alternatively, the sub-modules of FIG. 2 may be implemented utilizing an off-the-shelf PC with a single processor or multiple processors, with the functional operations distributed between the processors. As a further option, the sub-modules of FIG. 2 may be implemented utilizing a hybrid configuration in which certain modular functions are performed utilizing dedicated hardware, while the remaining modular functions are performed utilizing an off-the-shelf PC and the like. The sub-modules also may be implemented as software modules within a processing unit.

The operations of the sub-modules illustrated in FIG. 2 may be controlled by a local ultrasound controller 50 or by the processor module 36. The sub-modules 52-62 perform mid-processor operations. The ultrasound processor module 36 may receive ultrasound data 70 in one of several forms. In the embodiment of FIG. 2, the received ultrasound data 70 constitutes IQ data pairs representing the real and imaginary components associated with each data sample. The IQ data pairs are provided to one or more sub-modules, for example, a color-flow sub-module 52, a power Doppler sub-module 54, a B-mode sub-module 56, a spectral Doppler sub-module 58 and an M-mode sub-module 60. Other sub-modules may be included, such as a Tissue Doppler (TDE) sub-module 62, among others.

Each of sub-modules 52-62 are configured to process the IQ data pairs in a corresponding manner to generate color-flow data 72, power Doppler data 74, B-mode data 76, spectral Doppler data 78, M-mode data 80, and tissue Doppler data 82, among others, all of which may be stored in a memory 90 (or memory 34 or image memory 40 shown in FIG. 1) temporarily before subsequent processing. The data 72-82 may be stored, for example, as sets of vector data values, where each set defines an individual ultrasound image frame. The vector data values are generally organized based on the polar coordinate system.

A scan converter sub-module 92 accesses and obtains from the memory 90 the vector data values associated with an image frame and converts the set of vector data values to Cartesian coordinates to generate an ultrasound image frame 93 formatted for display. The ultrasound image frames 93 generated by the scan converter sub-module 92 may be provided back to the memory 90 for subsequent processing or may be provided to the memory 34 or the image memory 40.

Once the scan converter sub-module 92 generates the ultrasound image frames 93 associated with the data, the image frames may be restored in the memory 90 or communicated over a bus 96 to a database (not shown), the memory 34, the image memory 40 and/or to other processors (not shown).

As an example, it may be desired to view different ultrasound images in real-time on the display 38 (shown in FIG. 1). To do so, the scan converter sub-module 92 obtains data sets for images stored in the memory 90 of that are currently being acquired. The vector data is interpolated where necessary and converted into an X,Y format for video display to produce ultrasound image frames. The scan converted ultrasound image frames are provided to a display controller (not shown) that may include a video processor that maps the video to a gray-scale mapping for video display. The gray-scale map may represent a transfer function of the raw image data to displayed gray levels. Once the video data is mapped to the gray-scale values, the display controller controls the display 38, which may include one or more monitors or windows of the display, to display the image frame. The image displayed in the display 38 is produced from an image frame of data in which each datum indicates the intensity or brightness of a respective pixel in the display.

Referring again to FIG. 2, a 2D video processor sub-module 94 may be used to combine one or more of the frames generated from the different types of ultrasound information. For example, the 2D video processor sub-module 94 may combine different image frames by mapping one type of data to a gray map and mapping the other type of data to a color map for video display. In the final displayed image, the color pixel data is superimposed on the gray scale pixel data to form a single multi-mode image frame 98 that is again re-stored in the memory 90 or communicated over the bus 96. Successive frames of images may be stored as a cine loop (4D images) in the memory 90 or memory 40 (shown in FIG. 1). The cine loop represents a first in, first out circular image buffer to capture image data that is displayed in real-time to the user. The user may freeze the cine loop by entering a freeze command at the user interface 42. The user interface 42 may include, for example, a keyboard and mouse and all other input controls associated with inputting information into the ultrasound system 20 (shown in FIG. 1).

A 3D processor sub-module 100 is also controlled by the user interface 42 and accesses the memory 90 to obtain spatially consecutive groups of ultrasound image frames and to generate three dimensional image representations thereof, such as through volume rendering or surface rendering algorithms as are known. The three dimensional images may be generated utilizing various imaging techniques, such as ray-casting, maximum intensity pixel projection and the like.

Figure 3:
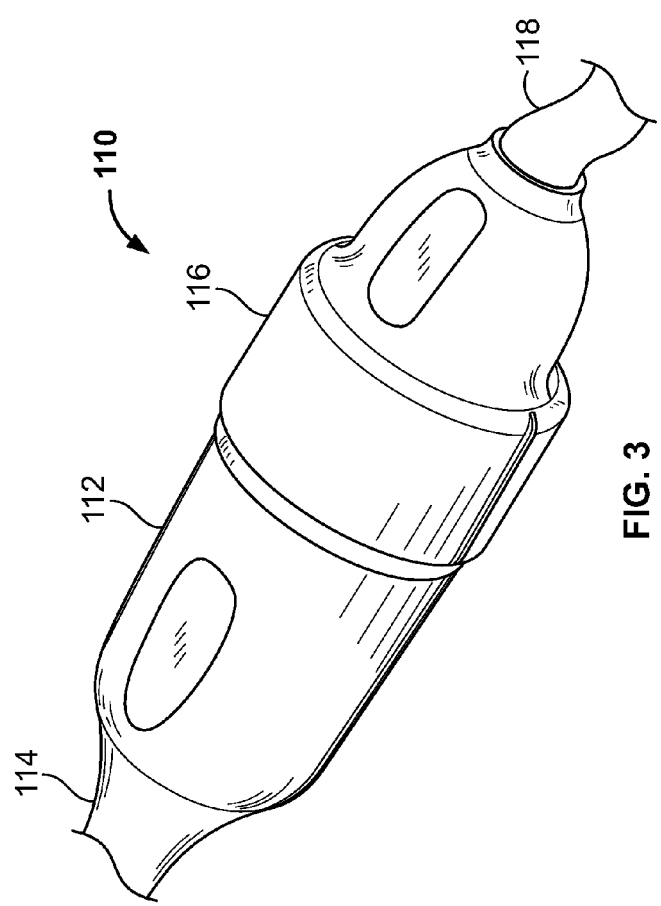
FIG. 3 is a perspective view of a connector system formed in accordance with various embodiments of the invention.
Figure 4:
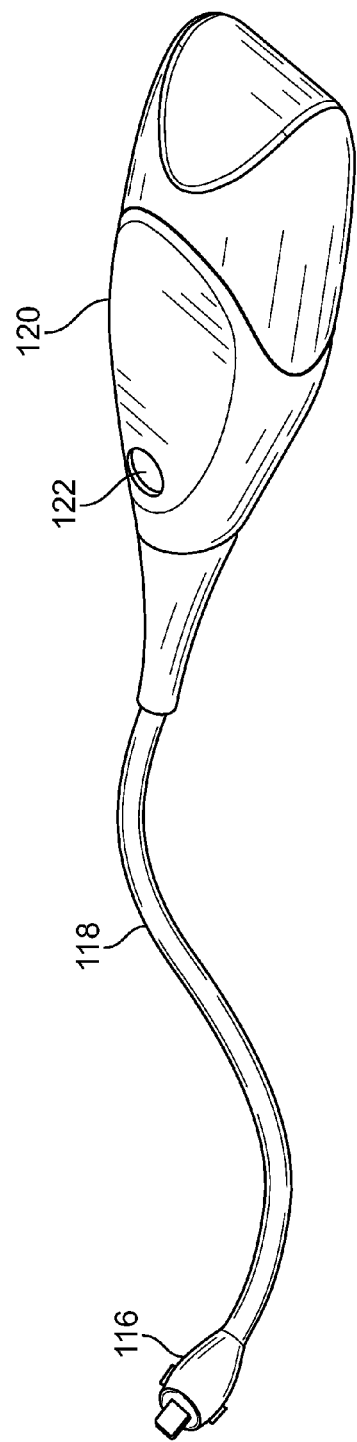
FIG. 4 is a perspective view of an ultrasound probe having a plug portion that may form part of a connector system in accordance with various embodiments of the invention.

Various embodiments of the invention provide a connector system 110 as shown in FIG. 3. The connector system 110 includes a receptacle portion 112 that is provided in combination with (e.g., is part of or at an end of) one cable. For example, the receptacle portion 112 may be provided at an end of an extension or umbilical cable 114 that connects, for example, to the ultrasound system 20 (shown in FIG. 1). The receptacle portion has a spring loaded engagement portion actuated by a rotational mechanism as described in more detail herein. The connector system 110 also includes a plug portion 116 that is provided in combination with (e.g., is part of or at an end of) another cable that is to be interconnected with the cable provided in combination with the receptacle portion 112. For example, the plug portion 116 may be provided at an end of a probe cable 118 that forms part of an ultrasound probe, for example, the ultrasound probe 120 shown in FIG. 4. The connector system 110 provides mating connection of the receptacle portion 112 and the plug portion 116 to, for example, couple the ultrasound probe 120 to the ultrasound system 20. It should be noted that the ultrasound probe 120 may be any type or kind or ultrasound probe for acquiring ultrasound information. The ultrasound probe 120 may include one or more controls 122 (e.g., buttons, knobs, etc.) thereon for controlling operation of the ultrasound probe 120 (e.g., on/off operation, mode selection, etc.).

It should be noted that the various embodiments of the connector system 110 are not limited to being provided in combination with a cable. For example, the connector system 110 or a portion thereof may be provided as part of a catheter or probe. As one example, the connector system 110 and, more particularly, the receptacle portion 112 may be provided as part of a housing, such as the system housing for a hand-carried system, or part of a housing for an electronics box, for example, an isolation or preamplifier module that is remote from the system and closer to an individual or patient.

Figure 5:
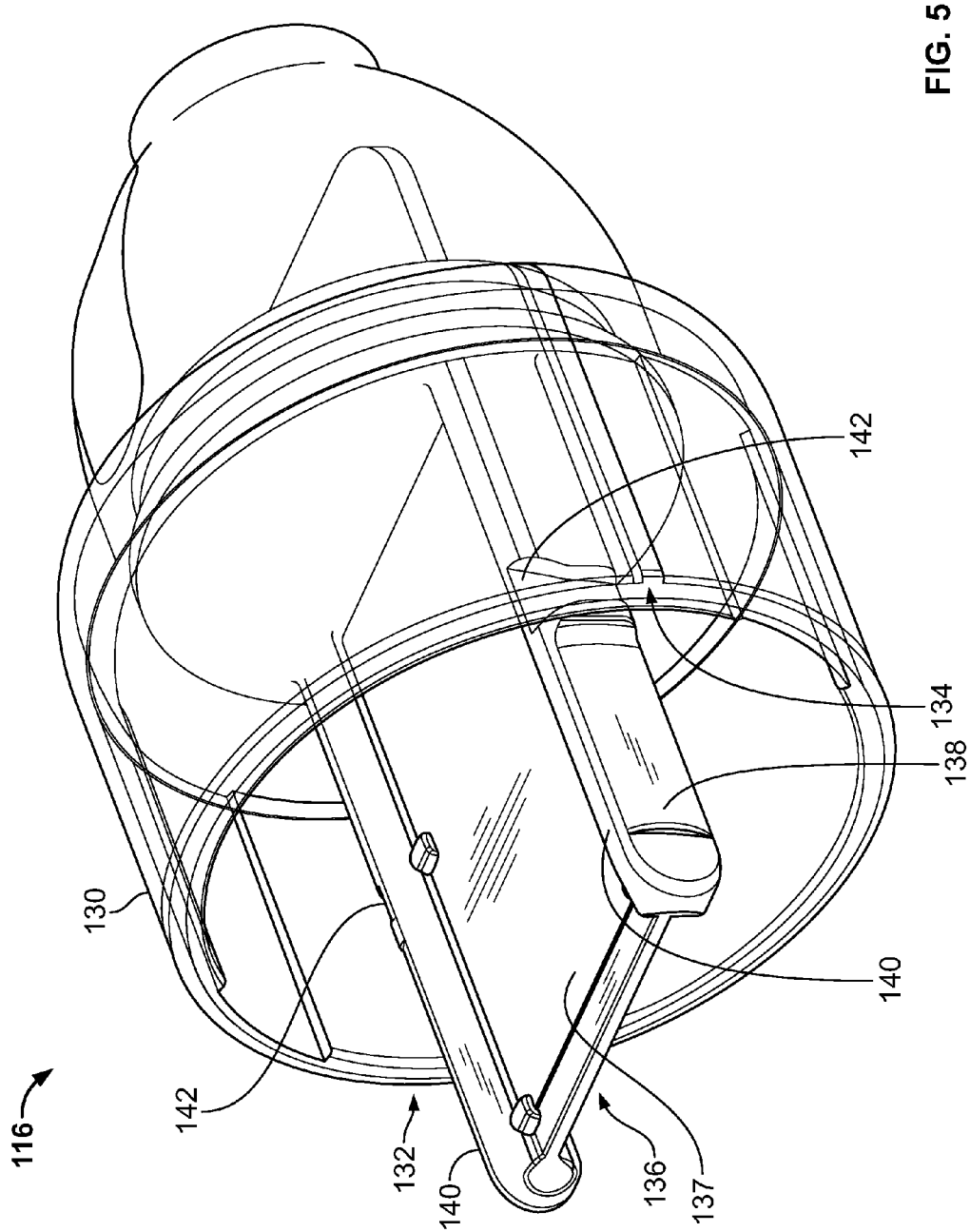
FIG. 5 is a perspective view of a plug portion of a connector system formed in accordance with various embodiments of the invention.

In one embodiment as shown in FIG. 5, the plug portion 116 includes a generally cylindrical shroud 130 along part of the plug portion 116 and that defines a cavity 132 therein. However, it should be noted that the plug portion 116 may be sized and shaped differently based on the size and shape of the receptacle portion 112 to provide mating connection therewith. Within the cavity 132 is a base portion 134 from which a connection member 136 extends. The connection member 136 may include a contact board 137, such as a printed circuit board (PCB), which may be a rigid PCB and defines an active area configured to communicate signals to and from the ultrasound probe 120. The contact board 137 also extends through the base portion 134 to allow connection of the contact board 137 with electronics within the ultrasound probe 120 as is known. It should be noted that the contact board 137 may be a rigid PCB, a flexible PCB wrapped around or attached to a rigid stiffener, or any type of connection member that can be electrically coupled to another electrical component.

In at least one embodiment the connection member 136 extends beyond the shroud 130 and outside the cavity 132. The connection member 136 also includes a frame 138 that is configured to allow sliding movement in one direction to engage the receptacle portion 112. For example, the frame 138 may include guides 140 that allow sliding movement in the x-direction and prevents movement in each of the y-direction and z-direction. The frame 138 also includes at least one locking slot 142 formed within the frame 138. In the embodiment shown, a locking slot 142 is provided on each longitudinal side of the frame 138. The frame 138 is generally formed along the periphery of the contact board 137 that extends from the base portion 134 and along the edge of the contact board 137.

Figure 6:
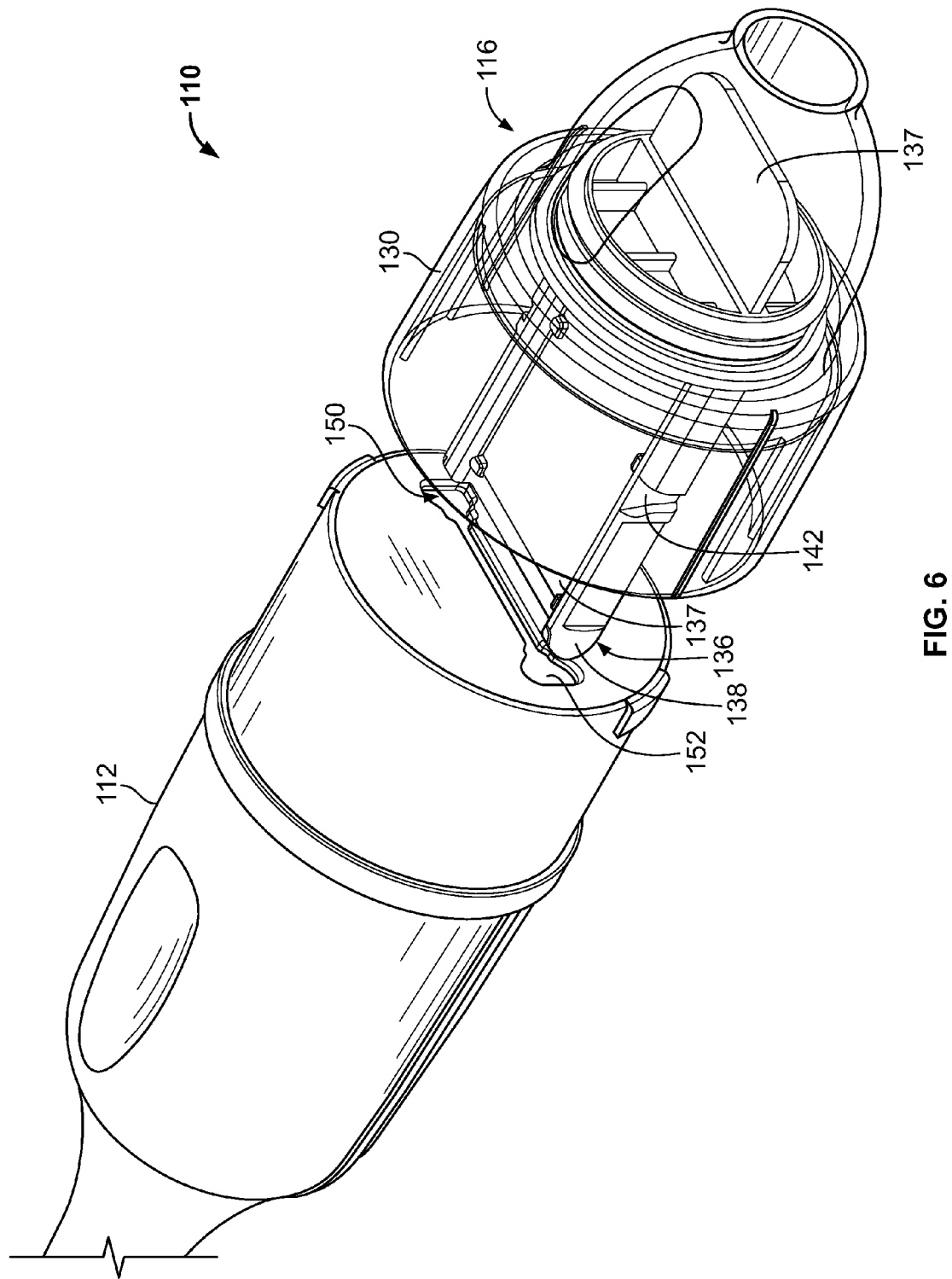
FIG. 6 is a perspective view of a plug portion and a receptacle portion that form a connector system in accordance with various embodiments of the invention.
Figure 7:
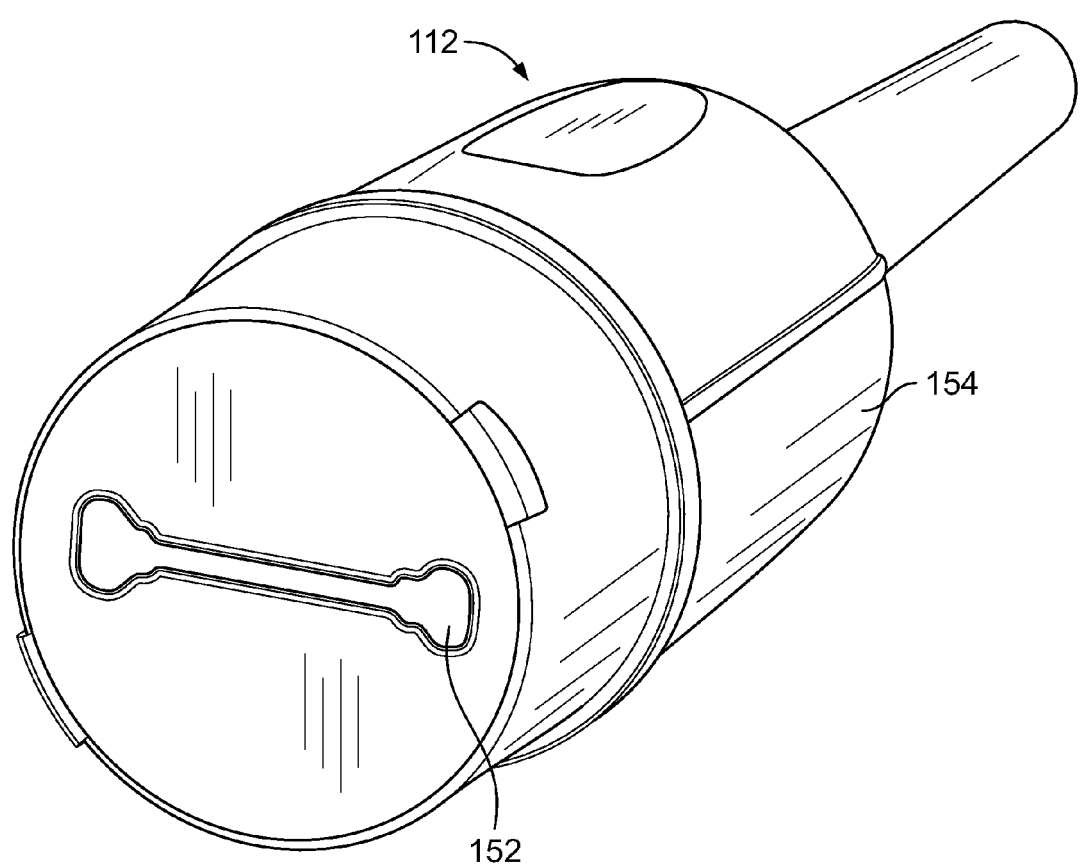
FIG. 7 is a perspective view of a receptacle portion of a connector system formed in accordance with various embodiments of the invention.

As shown in FIG. 6, the plug portion 116 with the connection member 136 is configured to engage the receptacle portion 112. In particular, the connection member 136 is configured to extend into the receptacle portion 112, and specifically, into an opening 150 that is covered by a cover 152. For example, the cover 152 may be a spring loaded door such that pressure applied to the cover 152 by the connection member 136 forces the cover 152 inward and allows the connection member 136 to pass therethrough into a housing 154 of the receptacle portion 112. Additionally, as shown in FIG. 7, the opening 150 and cover 152 are asymmetrically shaped to allow insertion of the connection member 136 in only one orientation. For example, the opening 150 and cover 152 are shaped such that one end is slightly larger (or wider) than the other end to allow insertion of the connection member 136 in only one orientation. Thus, the asymmetric shape prevents the connection member 136 from being inserted into the opening 150 in an orientation that that is, for example, 180 degrees from the desired connection arrangement. Different shapes and sizes of openings 150 and/or covers 152 may be provided, for example, for different connectors or ultrasound probes such that only certain plug portions 116 can be inserted into certain receptacle portions 112.

Figure 8:
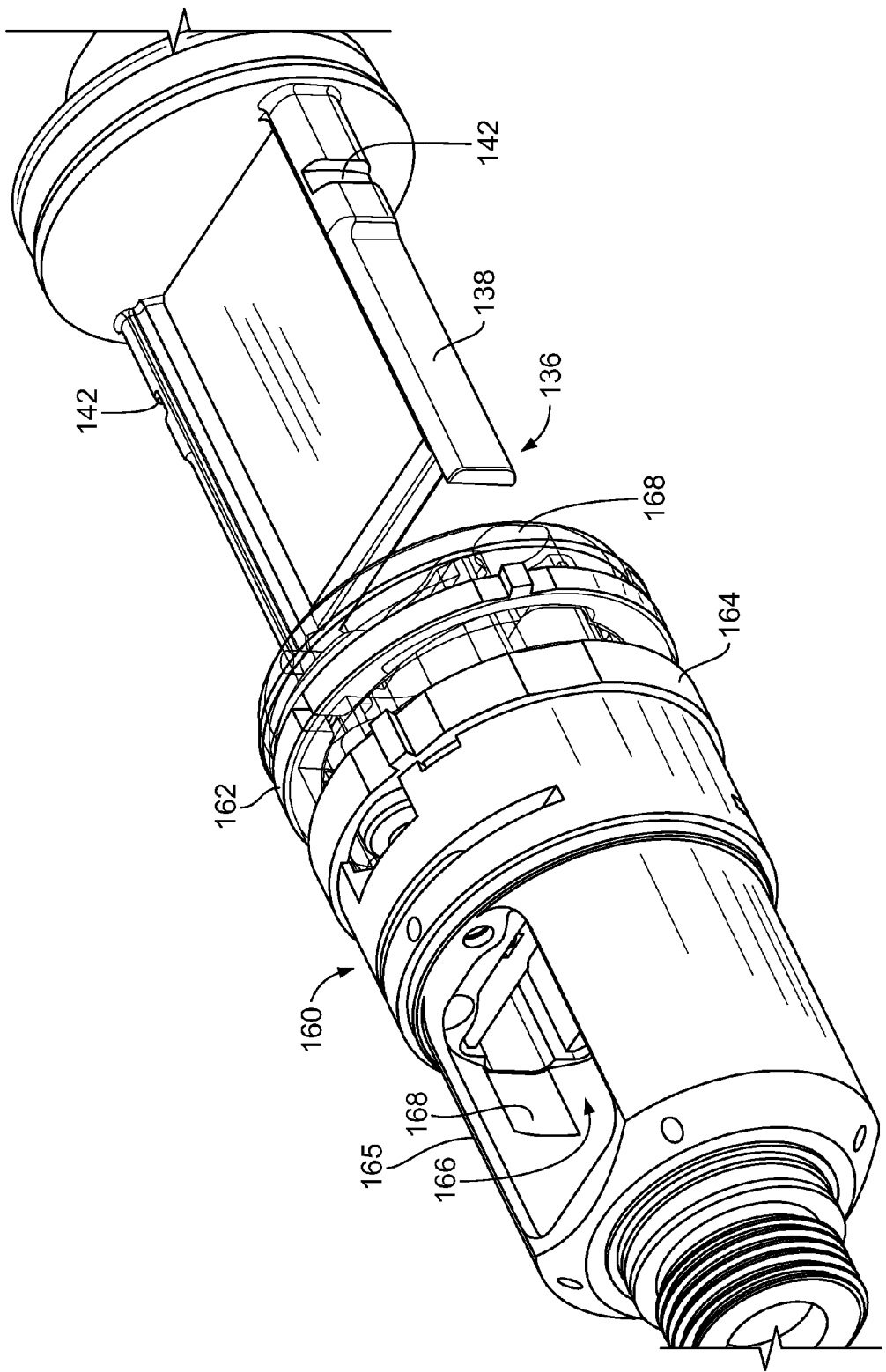
FIG. 8 is a perspective view of a plug portion and a receptacle portion without housings that form a connector system in accordance with various embodiments of the invention.

The connection member 136 is configured to engage spring loaded contact pins actuated by a rotating cam as described in more detail below. More particularly, as illustrated in FIG. 8 wherein the housing 154 of the receptacle portion 112 and the shroud 130 of the plug portion 116 are removed, the receptacle portion 112 includes therein an engagement and locking mechanism 160 having two different rings. Specifically, the engagement and locking mechanism 160 includes a control ring 162 and an engagement ring 164. The control ring 162 and engagement ring 164 in one embodiment are physically separate rings configured to rotate together when the housing 154 (shown in FIG. 7) of the receptacle portion 112 is rotated (e.g., twisted by a user).

The engagement and locking mechanism 160 includes a generally cylindrical body 165 having a cavity 166 extending along at least a portion of a length therein. A channel 168 extends along at least a portion of the length inside the cylindrical body 165 and is configured in one embodiment as a track for sliding engagement of the guides 140 of the frame 138 of the connection member 136 when inserted therein.

Figure 9:
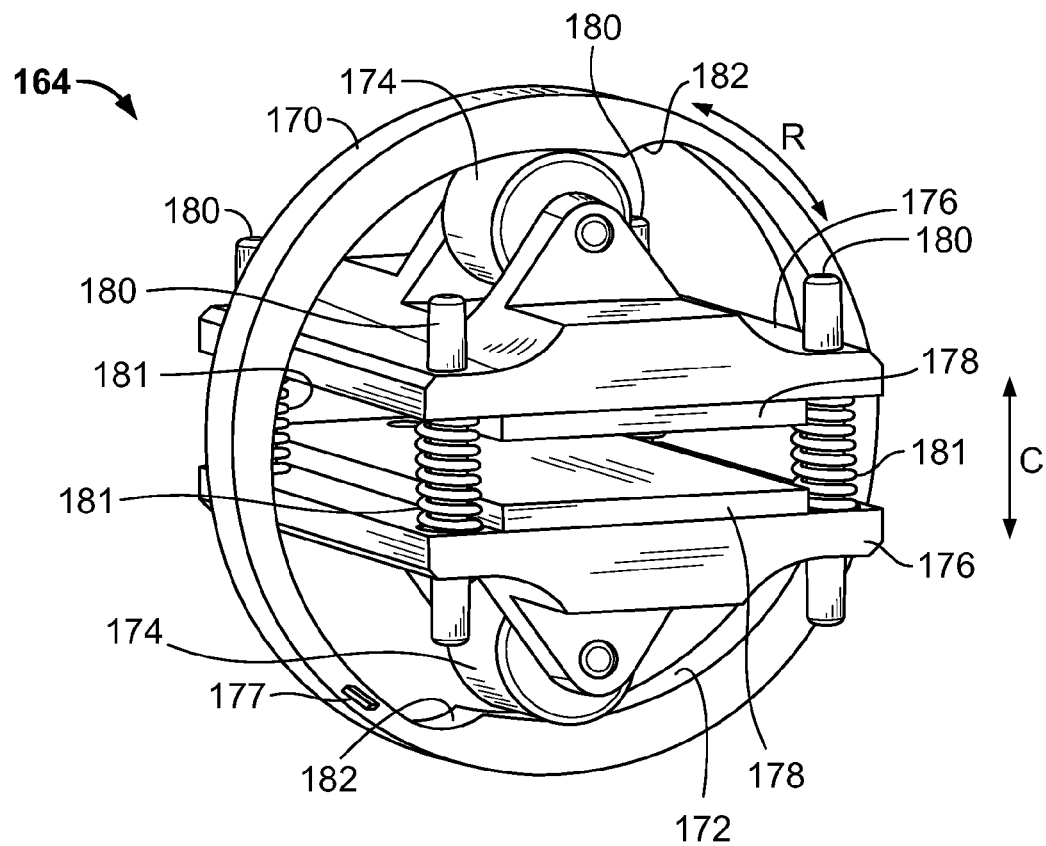
FIG. 9 is a perspective view of an engagement ring formed in accordance with various embodiments of the invention having opposing compression plates.

The engagement ring 164 includes a cam 170 as shown in FIG. 9 that is configured to be rotated as illustrated by the arrow R. An inner surface 172 of the cam 170 engages a pair of rollers 174 (e.g., rolling wheels) that are connected to opposing movable members 176. The movable members 176 are connected and configured to compress a pair of compression plates 178, which are illustrated as opposing compression plates 178. Guide pins 180 extend through each of the movable members 176, for example, one guide pin 180 at each corner of the movable member 176 to maintain the position and orientation of the movable members 176 during movement. A spring 181 or other compressible or biasing member is provided between the movable members 176 and along each of the guide pins 180 such that the compression plates 178 are movable as indicated by the arrow C.

The inner surface 172 of the cam 170 is shaped to allow movement of the pair of rollers 174 to a certain point, for example, to limit rotation thereof. In one embodiment, the profile or thickness of the inner surface 172 increases in the direction of rotation of the cam 170 that causes compression of the compression plates 178. The change in profile or thickness of the inner surface 172 is symmetric along each half of the inner surface 172 such that movement of the pair of rollers 174 is stopped at the thinnest part of the inner surface 172 along each half by the adjacent thickest part of the other half of the inner surface 172 that essentially defines stops 182 to prevent further rotation of the pair of rollers 174 and further opening of the compression plates 178. The stops 182 essentially limit clockwise rotation of the cam 170 and opening of the compression plates 178.

Figure 10:
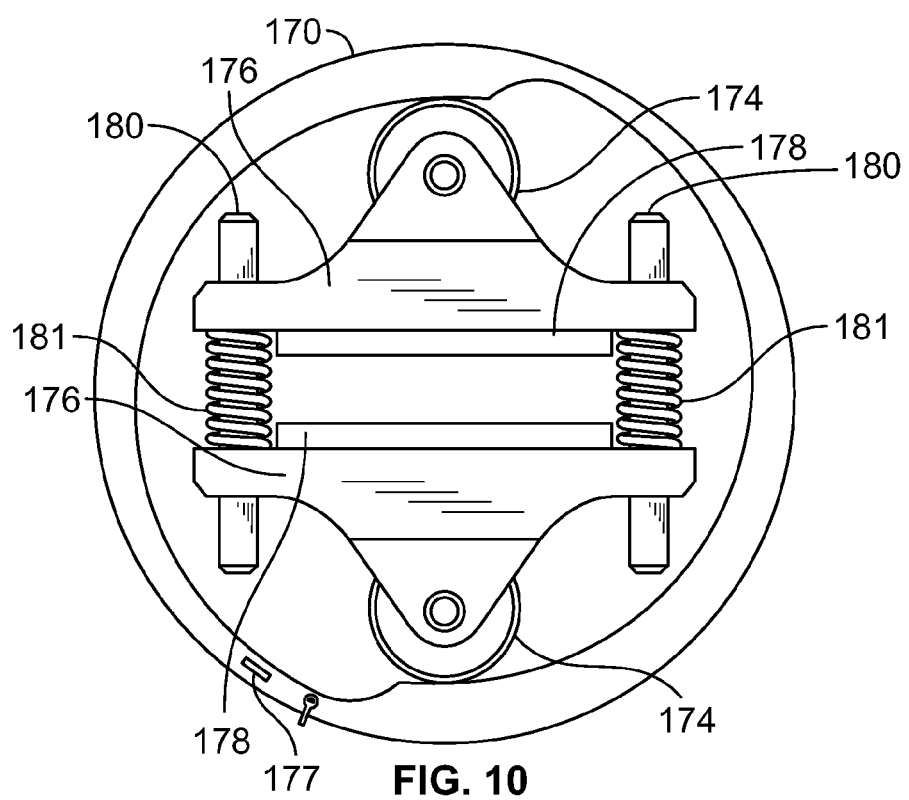
FIG. 10 is a side elevation view of the engagement ring of FIG. 9 showing the compression plates in a closed position.
Figure 11:
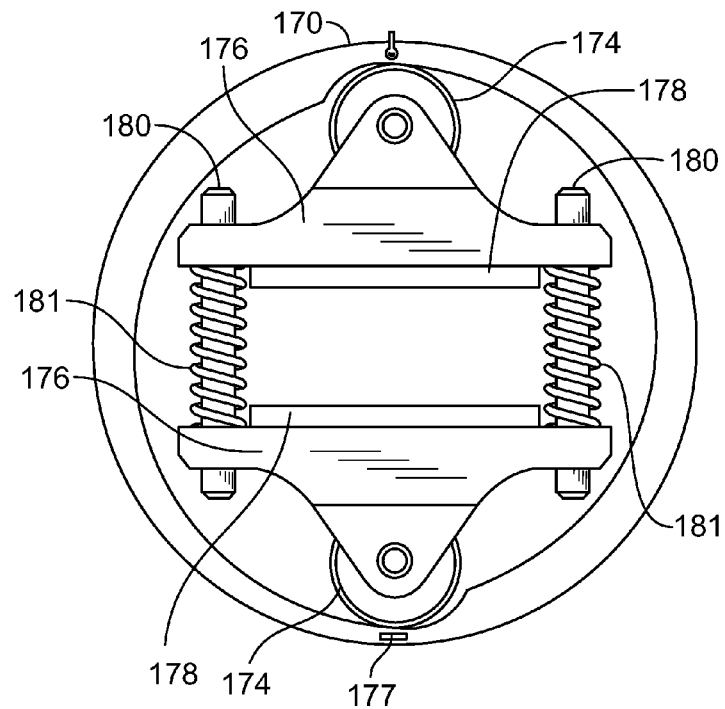
FIG. 11 is a side elevation view of the engagement ring of FIG. 9 showing the compression plates in an open position.

In operation, and as shown in FIGS. 10 and 11, rotation of the cam 170 causes movement of the movable members 176, thereby causing movement of the compression plates 178. In particular, as shown in FIG. 10, the compression plates 178 are illustrated in a compressed or closed state or position and in FIG. 11 the compression plates are illustrated in an uncompressed or open state or position. The force of the springs 181 facilitate movement from the compressed state to the uncompressed state. The guide pins 180 act to guide the movements of the movable members 176 such that the orientation and positioning of the compression plates 178 is maintained. Also, the symmetric configuration of the cam 170 provides symmetric movement of the compression plates 178. It should be noted that the movement track defined by the inner surface 172 of the cam 170 may be allowed to expand and contract, for example, by forming the cam 170 of aluminum or other suitable material. For example, the cam 170 may be formed to allow distortion thereof, for example, elastically. Also, a rotation limiting element 177 may be provided that limits counter-clockwise rotation of the cam 170. For example, the rotation limiting element 177 may be a protrusion on a side surface of the cam 170.

Figure 13:
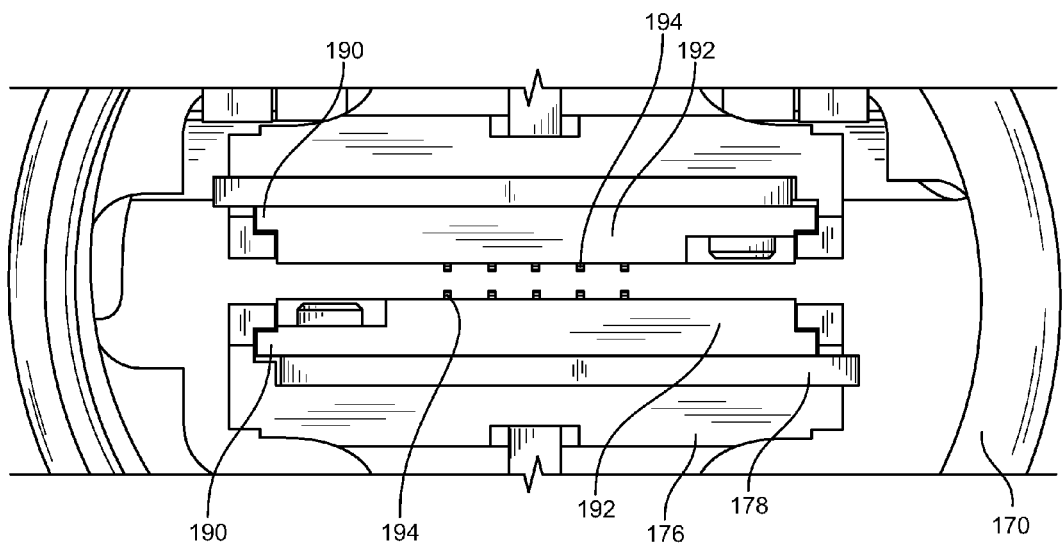
FIG. 13 is a side elevation view of compression plates formed in accordance with various embodiments of the invention coupled to interposers.
Figure 12:
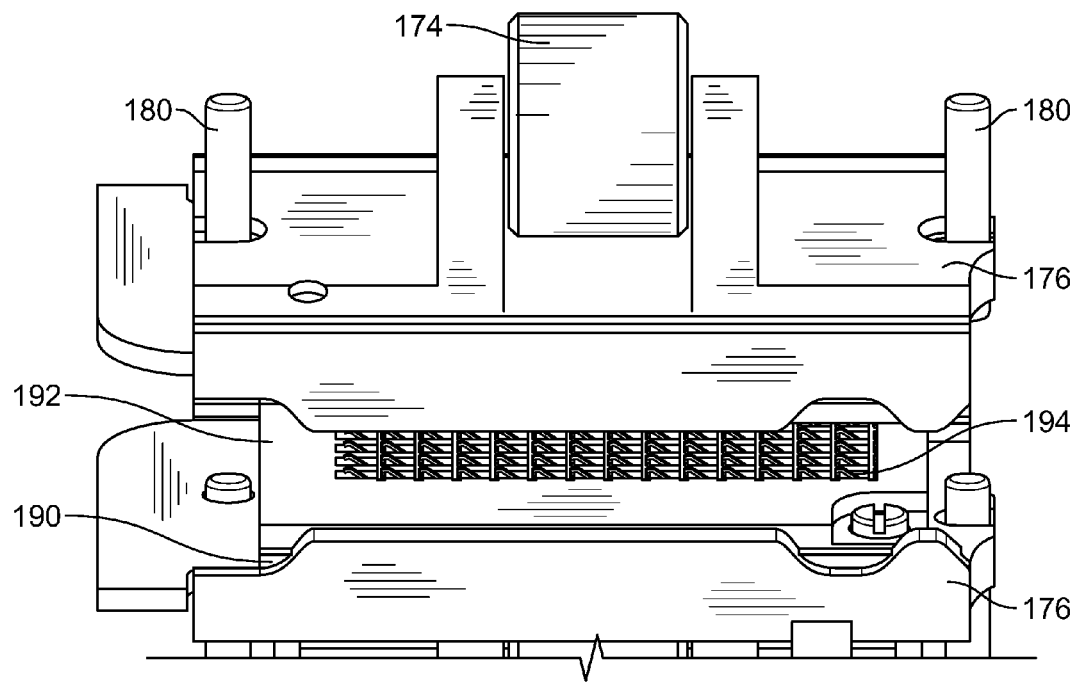
FIG. 12 is a perspective view of compression plates formed in accordance with various embodiments of the invention coupled to interposers.

It should be noted that other compression members or biasing elements may be provided in connection with the cam 170 and that replaces the springs 181. For example, a resilient clamp or tensioned coil may be used to provide bias to the movable members 176. Additionally, as shown in FIGS. 12 and 13, a printed circuit board (PCB) 190 may be coupled to each of the compression plates 178. Moreover, an interface 192 or contact plate, for example, an interposer plate may be connected to each of the PCBs 190 and that includes contact pins 194 that provide electrical connection with the connection member 136 of the plug portion 116 when inserted within the receptacle portion 112. For example, more than one-hundred contact pins 194 may be provided in an area of about fifteen millimeters by about twenty-five millimeters to provided connection between two high signal count cables. The stacking arrangement and coupling may be provided using any known process. It should be noted that the interface 192 may include, for example, an interposer having contact pins 194 that are not spring loaded and instead include any type of pin, anisotropic conductive file (ACF), or other electrical connection structure.

Figure 14:
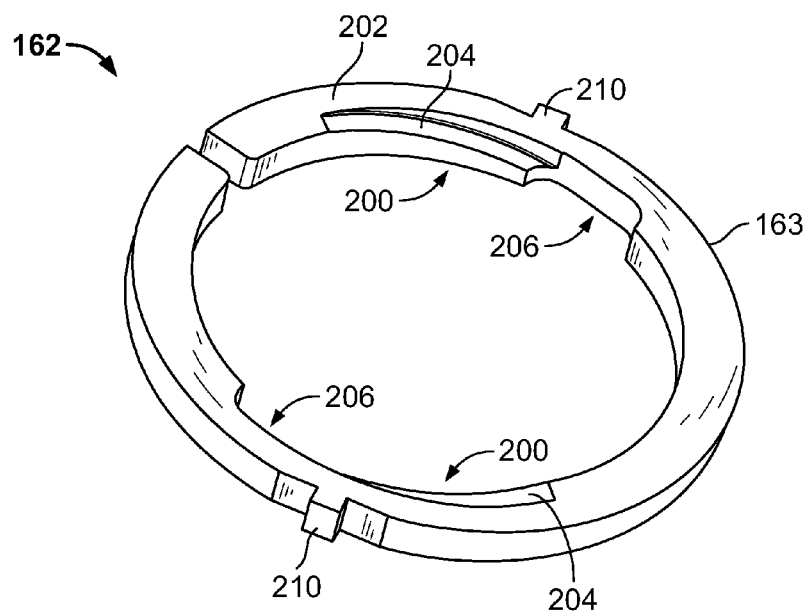
FIG. 14 is a perspective view of a control ring formed in accordance with various embodiments of the invention.

The engagement and locking mechanism 160 also includes the control ring 162 as shown in FIG. 14. The control ring 162 in one embodiment is a rotational cam 163 and includes a groove 200 along a portion of opposite sides of a side surface 202 of the control ring 162. The groove 200 is configured having a changing thickness to define a ramp 204. Accordingly, the change in thickness of the groove 200 defines an inclining or declining region forming the ramp 204. A notch 206 is provided at an end of the ramp 204, for example, at a lower or thinner end of the ramp 204. As described in more detail below, the ramp 204 is configured to engage the locking slot 142 of the frame 138 of the connection portion 136 within the plug portion 116. Rotation of the control ring 162 when engaged with the connection member 136 causes the frame 138 of the connection member 136 to be pulled into the receptacle portion 112 by the changing incline of the ramp 204 and as described in more detail below. The notch 206 is configured to allow insertion of the connection member 136 only when the compression plates 178 (shown in FIG. 9 though 11) are in an uncompressed or open state. The notch 206 also prevents too early contact-closing when inserting the connection member 136.

Figure 15:
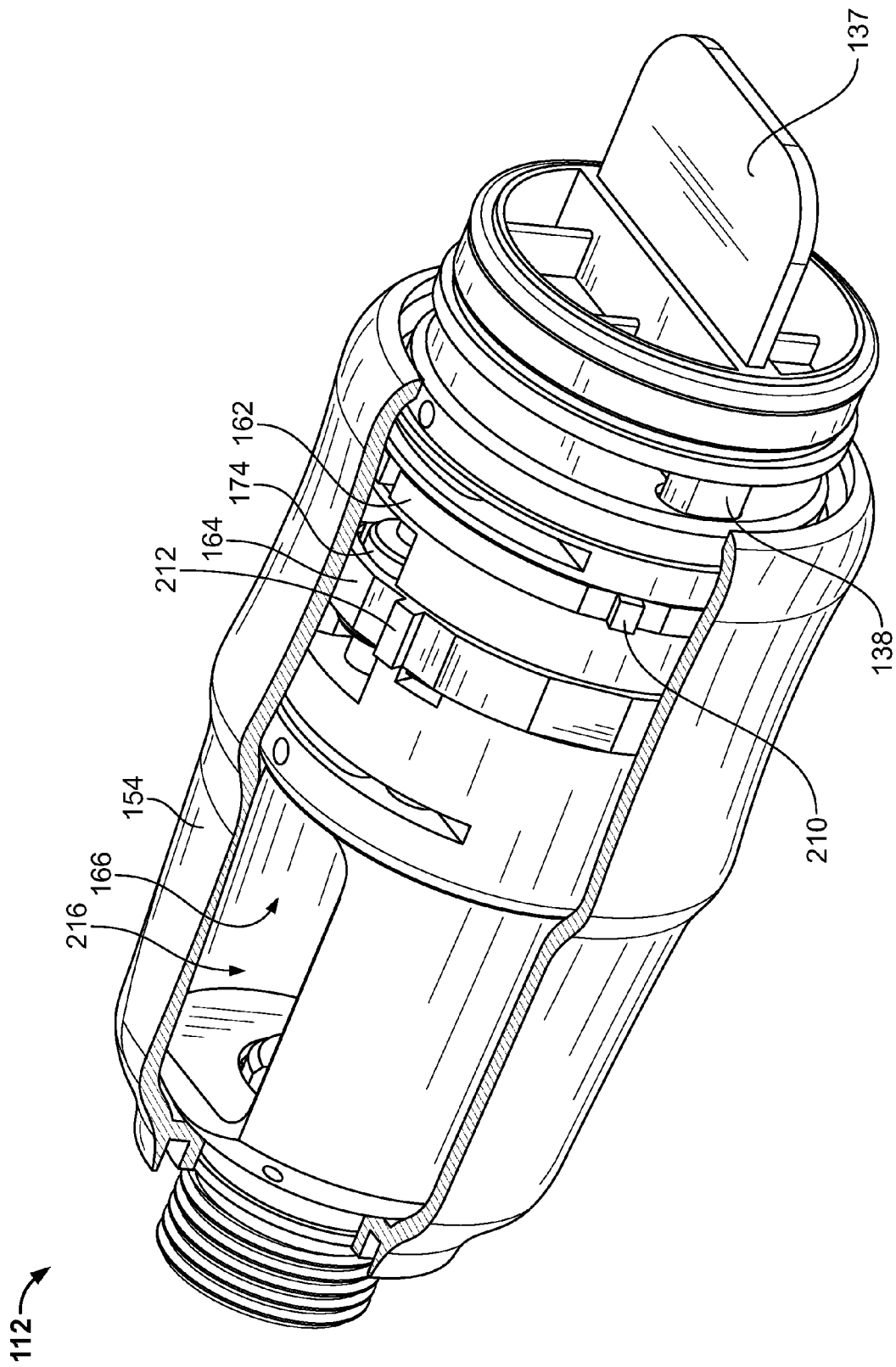
FIG. 15 is a perspective view of a receptacle portion formed in accordance with various embodiments of the invention with part of the housing removed.
Figure 16:
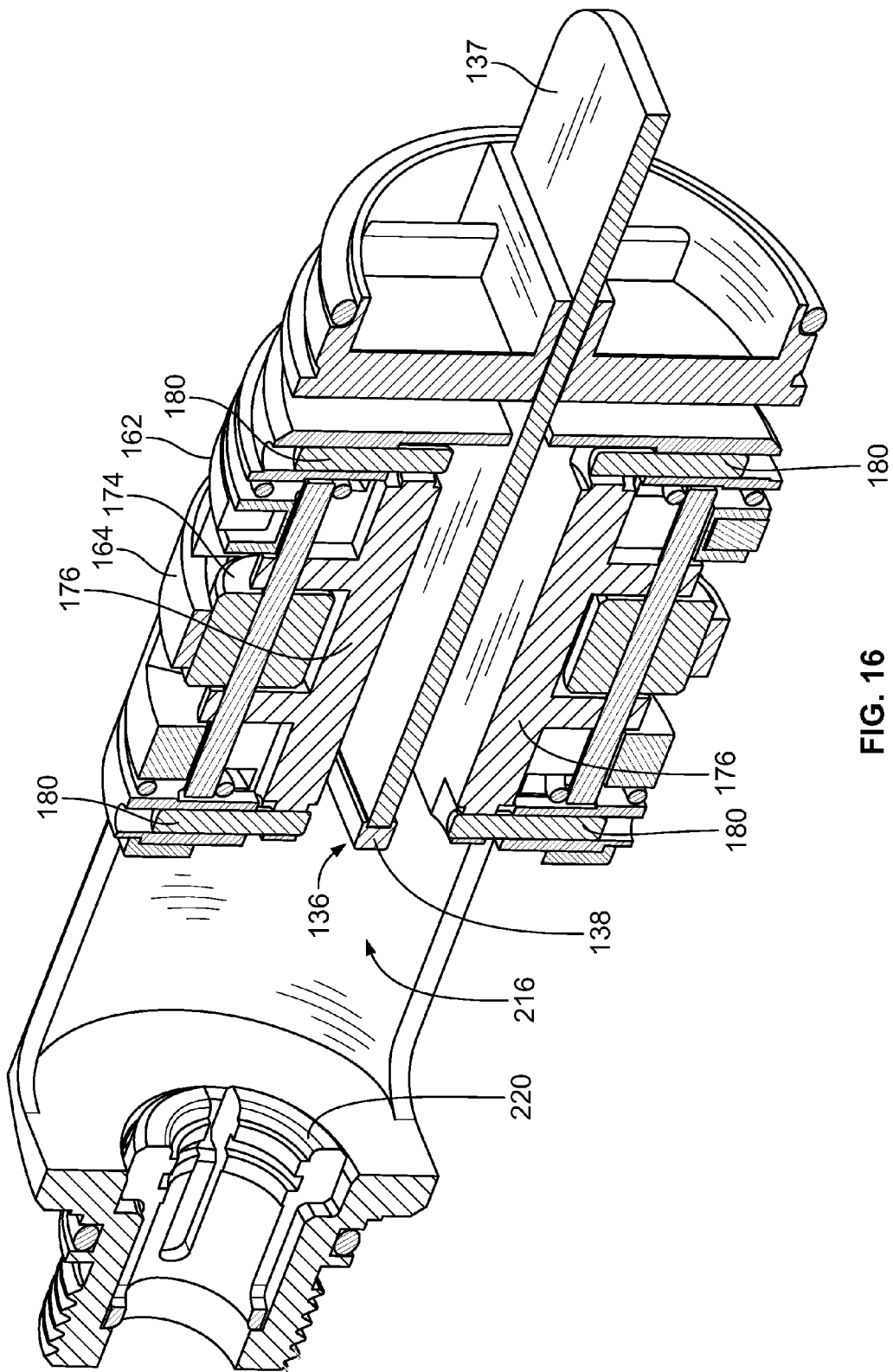
FIG. 16 is a cross-sectional view of a receptacle portion formed in accordance with various embodiments of the invention with the housing removed.

An engagement portion 210 may be provided on an outside surface of the control ring 162 to engage an interior of the housing 154 of the receptacle portion 112 as shown in FIG. 15 such that the control ring 162 rotates when the housing 154 is rotated. A similar engagement portion 212 may be provided on an outside surface of the engagement ring 164 (also shown in FIG. 15) to engage an interior of the housing 154 of the receptacle portion 112. Accordingly, the control ring 162 and engagement ring 164 may be aligned within the housing 154 with movement (e.g., rotation) of the control ring 162 and engagement ring 164 synchronized such that the amount of rotation of each of the control ring 162 and engagement ring 164 is the same when the housing 154 is rotated or twisted. It should be noted that a cavity 216 is also provided within the housing 154 and defines a cable service loop region for providing extra cable (e.g., a cable loop). Accordingly, if tension is provided to the cable 114 (shown in FIG. 3), excess cable from the cable loop allows the cable 114 to extend such that the cable is not disconnected from connections within the housing 154, for example, connections to a PCB (not shown). A cable stress relief member 220 as shown in FIG. 16 also may be provided to dissipate tension on the cable 114 through the components within the housing 154 to prevent or decrease the likelihood of damage to the components within the receptacle portion 112.

Figure 17:
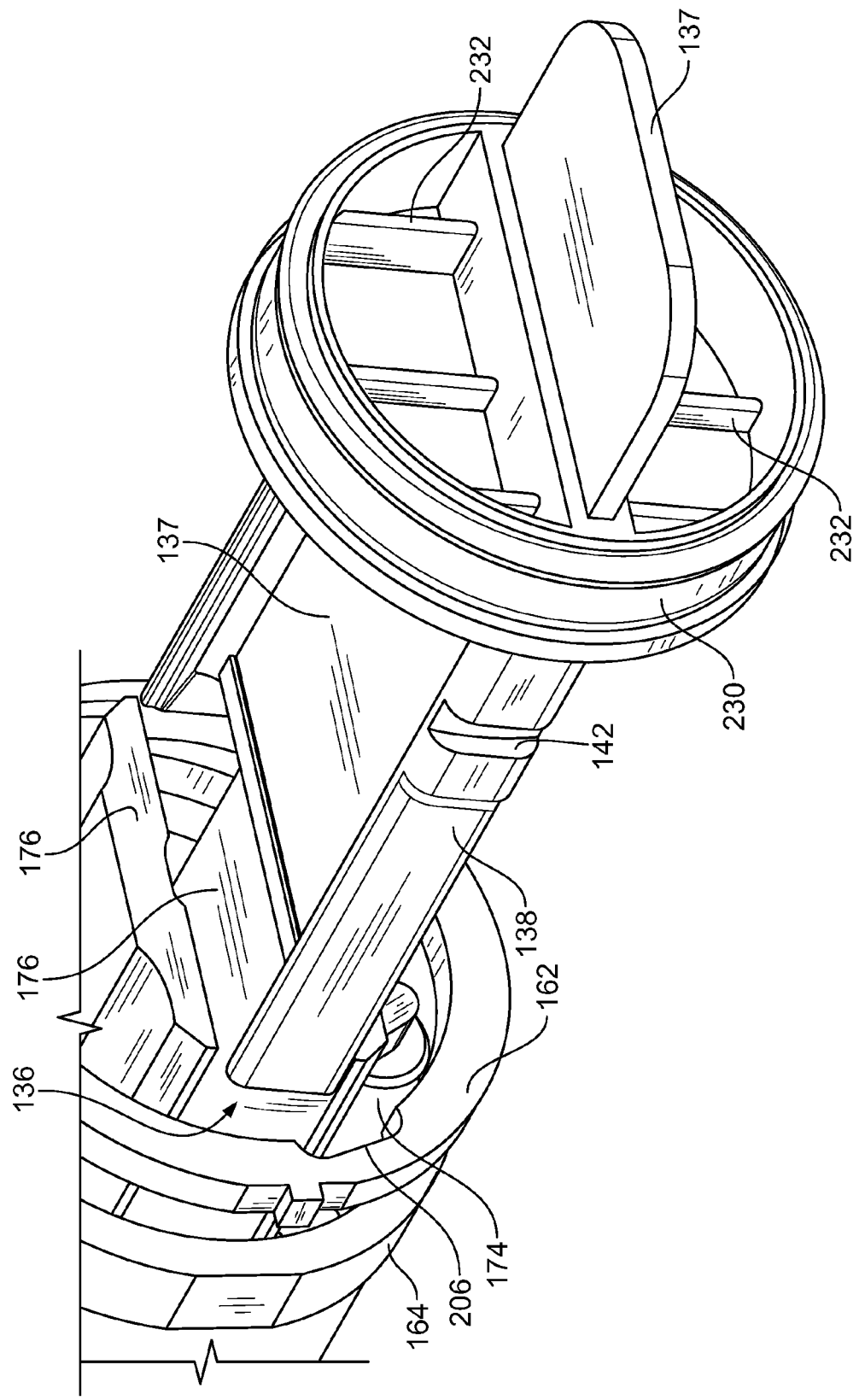
FIG. 17 is a perspective view of part of a receptacle portion formed in accordance with various embodiments of the invention with the housing removed.

Thus, in operation, and as shown in FIG. 17, the notch 206 of the control ring 162 (that turns with the housing 154) aligns with the frame 138 at only one rotation angle of the control ring 162, which is when the movable members 176 are in the uncompressed or opened state. If the control ring 162 is not rotated to this open position, the notch 206 is not aligned with the frame 138, which prevents the connection member 136 from being inserted within the receptacle portion 112. It should be noted that the plug portion 116 may include annular stiffening members 230 and vertical stiffening members 232.

Figure 18:
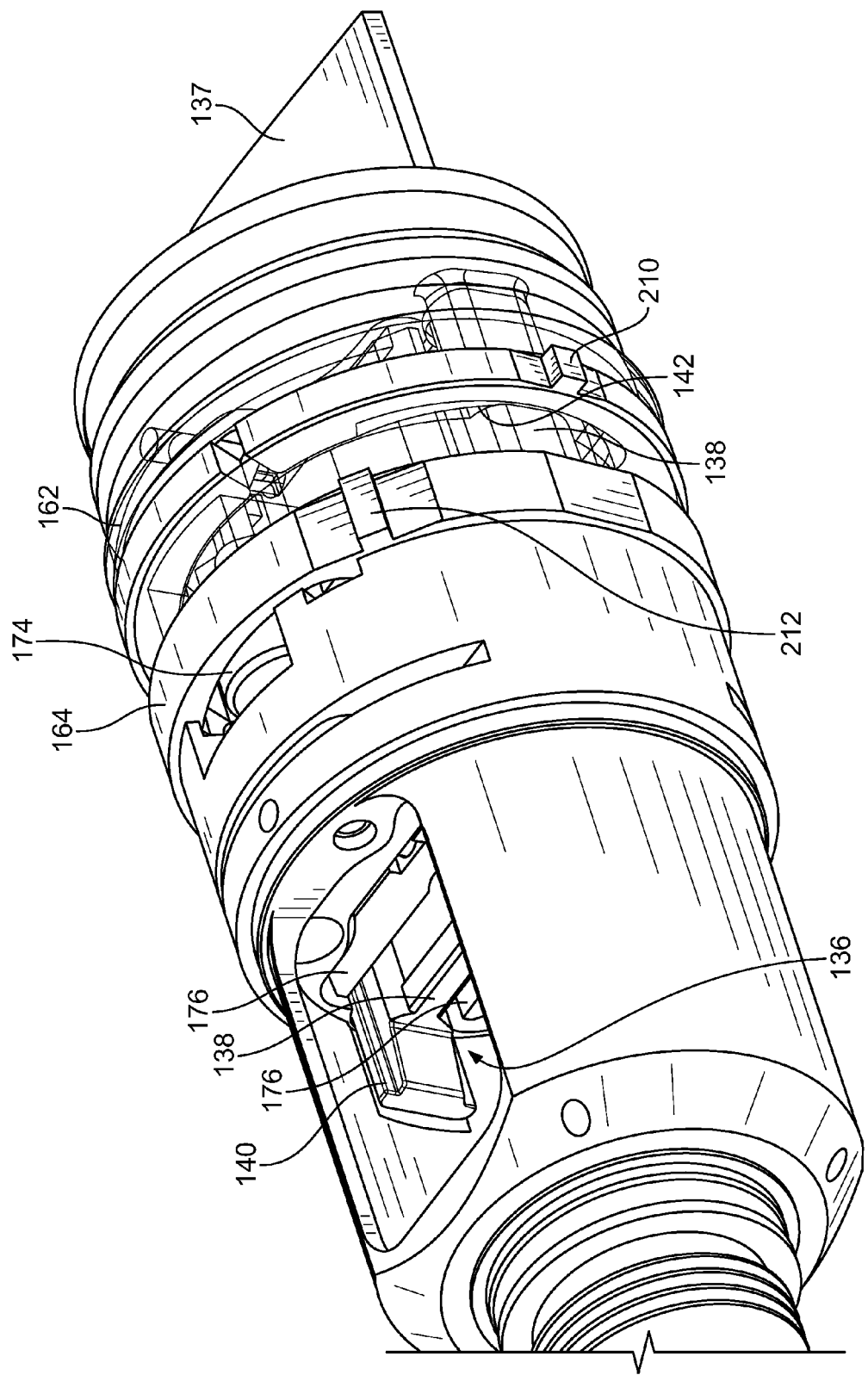
FIG. 18 is a perspective view of part of a receptacle portion formed in accordance with various embodiments of the invention with the housing removed and illustrating one rotational position of the receptacle portion.
Figure 19:
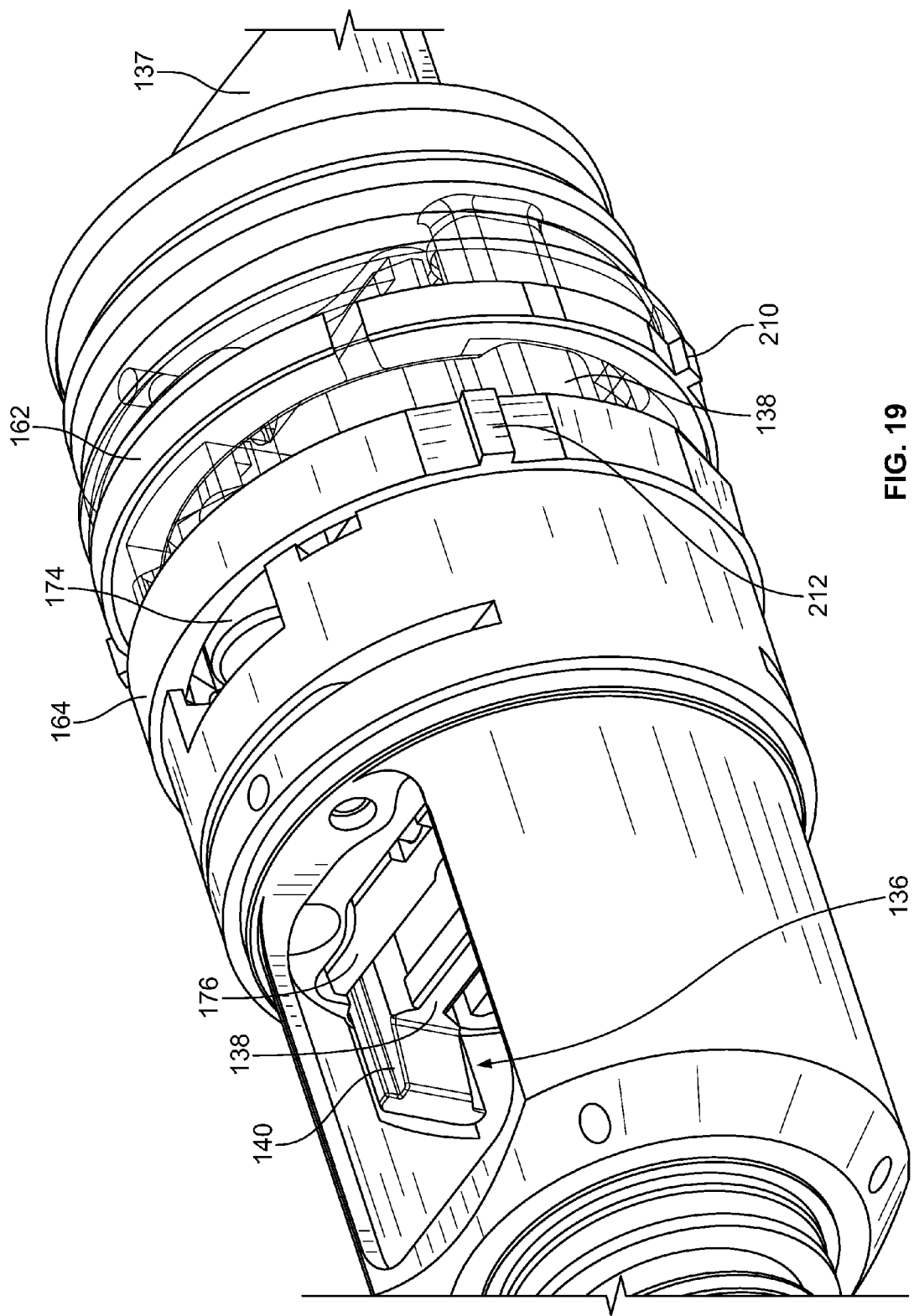
FIG. 19 is a perspective view of part of a receptacle portion formed in accordance with various embodiments of the invention with the housing removed and illustrating another rotational position of the receptacle portion.
Figure 20:
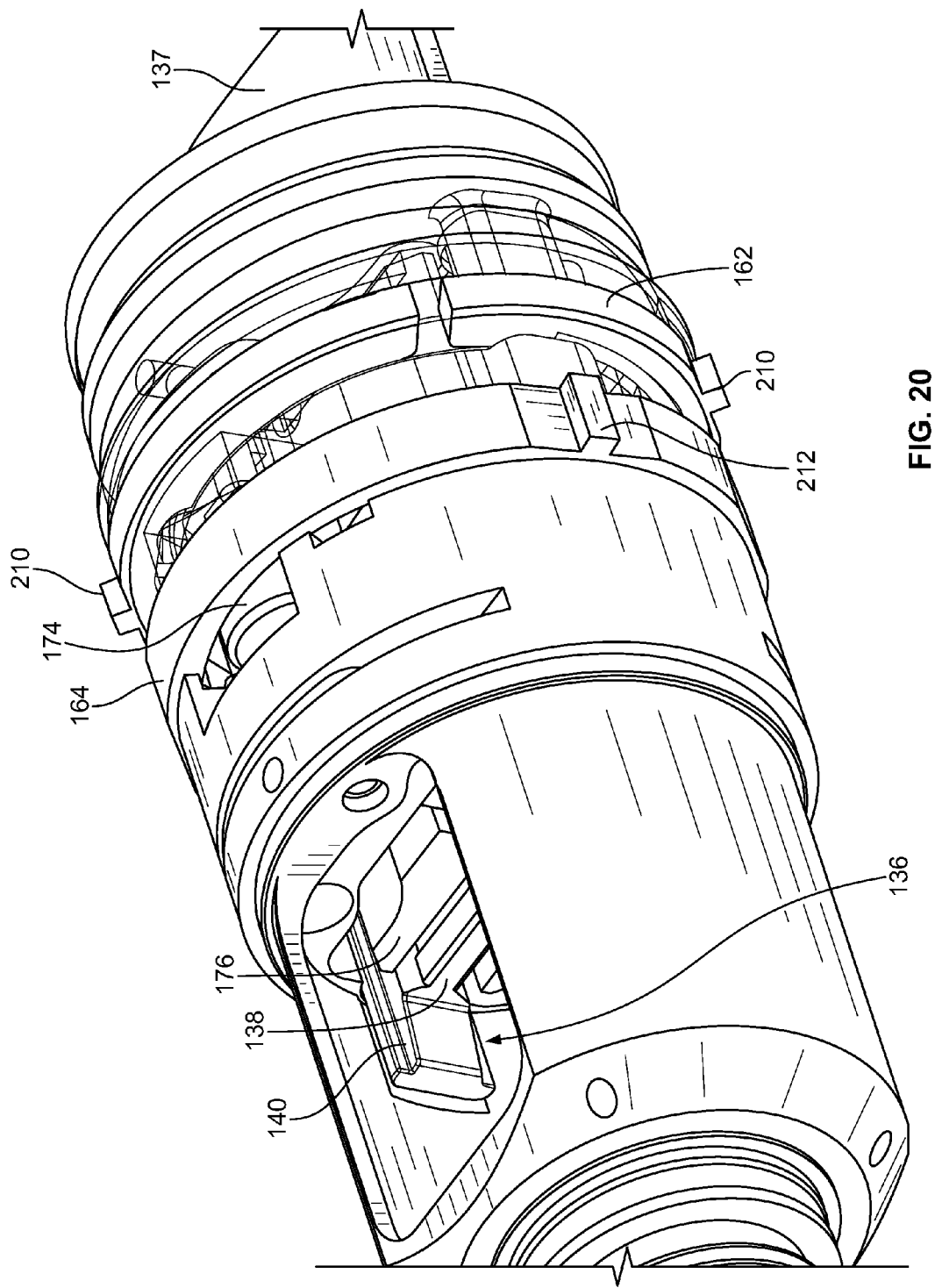
FIG. 20 is a perspective view of part of a receptacle portion formed in accordance with various embodiments of the invention with the housing removed and illustrating another rotational position of the receptacle portion.

Once the connection member 136 is inserted within the receptacle portion 112, the housing 154 is rotated as shown in FIGS. 18 through 20. As can be seen, the ramps 204 of the control ring 162 pulls the connection member 136 with the contact board 137 into the receptacle portion 112 and aligns the contact board between the movable members 176. The ramps 204 engage the locking slots 142 formed within the frame 138. The channels 168 limit the movement of the connection member 136 to translation in the x-direction as the rails 140 of the frame 138 slide within the channels 168. As the control ring 162 and engagement ring 164 are further rotated as shown in FIG. 19, the control ring 162, which is guided in a circular track by the locking slots 142, causes movement of the connection member 136 in the x-direction within the receptacle portion 112. It should be noted that the notch 206 of the control ring 162 has rotated out of the locking slots 142. At the same time the movable members 176 are compressed by rotation of the engagement ring 164.

As the control ring 162 and engagement ring 164 are even further rotated as shown in FIG. 20 it should be noted that the positioning of the connection member 136 and the contact board 137 between the movable members 176 is completed before the contact pins 194 of the interface 192 (shown in FIGS. 12 and 13) engage complementary portions on the contact board 137. Thus, electrical contact may be made to both sides of the contact board using, for example, the interposer plates on each of the compression plates 178.

Accordingly, various embodiments provide two contact plates that are movable using a rotatable cam. The rotatable cam actuates contact plates such that the contact plates are moved toward each other. A connection member is aligned between the contact plates using a control ring. For example, a rigid PCB may be inserted into the gap between the contact plates and electrical connection is provided therewith when the contact plates (having electrical pins) are compressed and engage the rigid PCB.

At least one technical effect of the various embodiments of the connector system described herein includes providing two-sided contact on a plug connector, for example, of an ultrasound probe having a high signal count. Alignment and electrical connection is accomplished using two rotating rings allowing connection of high density and miniaturized connectors. The rotating rings may be configured as cams to allow a user to more easily overcome the increased contact force that is caused by a high number of spring loaded interposer pins. Blocking features also prevent improper connection, such as reverse oriented insertion of the plug.

It also should be noted that the various embodiments may be implemented in connection with different types and kinds of ultrasound systems. For example, a 3D-capable miniaturized ultrasound imaging system, a hand carried or pocket-sized ultrasound imaging system, a console-based ultrasound imaging system, etc. In general, the various embodiments may be implemented in any system wherein electrical connection, for example, of two high signal count cables is desired or needed.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A receptacle for a connector system having a plug, the receptacle comprising:
    at least one rotatable member configured to have a cavity; and
    a pair of opposing compression plates located at least partially within the cavity, the at least one rotatable member configured to move the opposing compression plates as the rotatable member rotates, the compression plates causing contact with a portion of the plug inserted between the compression plates.

2. A receptacle in accordance with claim 1 wherein the at least one rotatable member comprises a rotatable cam.

3. A receptacle in accordance with claim 1 further comprising at least one biasing member to bias the pair of opposing compression plates.

4. A receptacle in accordance with claim 1 further comprising an interposer coupled to at least one of the compression plates.

5. A receptacle in accordance with claim 1 wherein the at least one rotatable member has a varying thickness.

6. A receptacle in accordance with claim 1 wherein the at least one rotatable member comprises two physically separate cams, with one of the cams configured to move the compression plates and the other cam configured to align the portion of the plug between the compression plates.

7. A receptacle in accordance with claim 6 further comprising a housing and wherein the two physically separate cams are each coupled to the housing to synchronize movement thereof.

8. A receptacle in accordance with claim 1 further comprising a generally cylindrical body having a channel extending along a length thereof and configured to slidingly engage a connection portion of the plug.

9. A receptacle in accordance with claim 1 further comprising a housing comprising a spring loaded door configured to receive a portion of the plug having a complementary shape to a shape of an opening covered by the spring loaded door.

10. A receptacle in accordance with claim 1 further comprising a cable service loop region configured to receive therein extra length of cable.

11. A receptacle in accordance with claim 1 further comprising a rotatable member defining a control ring having a ramp portion configured to engage a slot of the portion of the plug.

12. A receptacle in accordance with claim 11 wherein the control ring is configured to move the plug toward the compression plates.

13. A receptacle in accordance with claim 1 further comprising a pair of rollers engaging the compression plates to move the compression plates as the rotatable member rotates and wherein contact with a portion of the plug inserted between the compression plates comprises two-sided contact with the portion of the plug.

14. A connector system comprising:
    a plug portion having a connection member; and
    a receptacle portion configured to engage the plug portion, the receptacle portion having rotationally actuated contact plates located within a housing, the contact plates movable to engage the connection member of the plug portion between the contact plates when the housing is at least partially rotated.

15. A connector system in accordance with claim 14 wherein the connection member comprises contacts on at least one side and the receptacle portion comprises at least one rotating cam configured to rotate when the housing is rotated, the at least one rotating cam moving the rotationally actuated contact plates to cause at least one of the contact plates to engage the contacts.

16. A connector system in accordance with claim 14 wherein the receptacle portion further comprises at least one rotating cam moving a connection member of the plug in alignment with the contact plates.

17. A connector system in accordance with claim 14 wherein the housing of the receptacle portion comprises an asymmetrically shaped opening for receiving therein a connection member of the plug portion having a complementary asymmetrical shape.

18. A connector system in accordance with claim 17 further comprising a spring loaded cover covering the asymmetrically shaped opening.

19. A connector system in accordance with claim 14 wherein the plug portion is connected to one end of an ultrasound probe and the receptacle portion is connected to one end of an umbilical cord of an ultrasound system.

20. An ultrasound system comprising:
    a control portion having an umbilical cable connected thereto, the umbilical cable having a receptacle providing high signal count communication, the receptacle having a rotational actuating mechanism configured to have a cavity and a pair of opposing compression plates located at least partially within the cavity; and
    an ultrasound probe having a probe cable connected thereto, the probe cable having a plug, and wherein interconnection of the umbilical cable with the probe cable via the receptacle and plug is actuated by the rotational actuating mechanism of the receptacle such that the compression plates engage a connection member of the plug between the compression plates.

* * * * *